United States Patent [19]

Lebacq

[11] Patent Number: 5,073,483

[45] Date of Patent: Dec. 17, 1991

[54] METHOD OF STAINING NUCLEIC ACIDS DETECTED BY NON-RADIOACTIVE LABELLING AND KIT OF REACTANTS FOR CARRYING OUT THE METHOD

[75] Inventor: Philippe Lebacq, Paris, France

[73] Assignee: Bioprobe Systems, Paris, France

[21] Appl. No.: 328,340

[22] Filed: Mar. 24, 1989

[30] Foreign Application Priority Data

Mar. 25, 1988 [FR] France .................. 88 03982
Mar. 10, 1989 [FR] France .................. 89 03191

[51] Int. Cl.$^5$ .................. C12Q 1/68; C12Q 1/34; C12Q 1/42; G01N 33/53
[52] U.S. Cl. .................. 435/6; 435/7.91; 435/18; 435/21; 536/27; 935/77; 935/78
[58] Field of Search .................. 435/6, 7, 7.91, 18, 435/21; 935/77, 78; 536/27

[56] References Cited

U.S. PATENT DOCUMENTS

| | | | |
|---|---|---|---|
| 4,313,734 | 2/1982 | Leuvering | 422/61 |
| 4,581,333 | 4/1986 | Kourilsky et al. | 435/7 |
| 4,775,631 | 10/1988 | Saman | 435/6 |

FOREIGN PATENT DOCUMENTS 0063879  3/1982  European Pat. Off. .

OTHER PUBLICATIONS

Chemical Abstract, vol. 101:1984, Abstract No. 16726f.
Colloidal Gold: Principles and Methods & Applications, vol. 2, Academic Press, N.Y., Chap 19, (1989), pp. 380-396.
Moeremans. G, (1984), Sensitive Visualization of Ag-Ab React in Dot and Blot Immune Ov . . . , J. Immunol. Meth 74:353-360.
Gribnau T. et al. (1986), Particle Labelled Immunoassay, Jou. of Chromat. 376:175-189.
Surekr Latzko (1984), Visualization of Antigenic Prot. Bloted onto Nitrocellulose Using Immun Au-Bioch. Bioph. Res. Com 121(1), 284-289.

Primary Examiner—Robert A. Wax
Assistant Examiner—Miguel H. Escallon
Attorney, Agent, or Firm—Dennison, Meserole, Pollack & Scheiner

[57] ABSTRACT

A method of staining a nucleic acid sequence which is fixed on a solid support is described wherein an enzymatic system which fixes this sequence is employed to detect it by non-radioactive labelling, the enzymatic system being subsequently reacted with chromogenic substrate to produce a colored product. A developer solution is used comprising a sulfur organic compound constituting the substrate which is adapted to be hydrolized by the enzyme to form an organic thiol, and a metallic compound, for example a gold compound. The metallic compound is soluble and stable in aqueous solution and can react with the organic thiol to form a metal-organic compound complex having a characteristic color which precipitates in situ, which metal-organic complex subsequently may be decolorized with a reducing agent to thus allow reuse of the solid support. A set, or kit, of reactants for carrying out the method also is disclosed.

16 Claims, No Drawings

METHOD OF STAINING NUCLEIC ACIDS DETECTED BY NON-RADIOACTIVE LABELLING AND KIT OF REACTANTS FOR CARRYING OUT THE METHOD

BACKGROUND OF THE INVENTION

1. Field of the Invention

The invention concerns staining of nucleic acids which have been fixed on a solid support and which are detected by a non-radioactive labelling method.

2. Description of the Prior Art

Detection of specific nucleic acid sequences in biological entities is becoming more and more important, particularly in detecting genetic illnesses.

Methods using solid supports are already known, for example the use of a polyamide or nitrocellulose membrane to which nucleic acids from a sample are transferred and fixed: the desired sequence may then be detected on the support.

The nucleic acid in a sample may be as natural or synthetic, modified or unmodified DNA or RNA. It is usually fragmented using restriction enzymes, the fragments subsequently being transferred and fixed onto the support by known means.

A particular sequence may then be identified using a detection system such as utilizing a "probe" which will fix itself specifically on the sequence and reveal it in situ, i.e. at the location of its fixation on the solid support.

Generally, the detection system employed comprises a sequence complementary to the sequence to be identified which can hybridize with the latter. Such hybridization only occurs when the detection system recognizes a complementary sequence held on the solid support.

Direct detection of nucleic acids is possible in certain methods without necessitating hybridization between a "target" sequence held on the solid support and a "probe" sequence forming part of the detection means.

Such nucleic acid detection, either directly or following hybridization of two complementary nucleic acid sequences, has been carried out for some time using radioactive isotopes. In methods of this type, one or more nucleosides radio-labelled with $^3H$ or $^{32}P$ are used to label the nucleic acids which are detected by counting or autoradiography. Whilst such known methods are reliable and sensitive, they unfortunately necessitate the use of laboratories specially equipped for using radioactivity. Further, such laboratories must have the required licences for handling, using and confining radioactive isotopes.

In order to overcome this drawback, detection methods which do not use radioactive isotopes have recently been developed.

One such method involves detection of nucleic acids which have previously been fixed on a solid support such as a membrane wherein an enzymatic system is employed to label the sequence non-radioactively and which is then reacted with a chromogenic substrate to form a colored product which precipitates in situ thus revealing the sequence at the reaction site.

Such detection methods are carried out using a set or "kit" of reactants containing those products necessary for characterizing specific nucleic acids.

Most commercially available nucleic acid detection kits use alkaline phosphatase as the final visual detection enzyme. Properties of this enzyme are such that non-radioactive detection methods using it are as sensitive as detection methods utilizing radioactive isotopes.

Alkaline phosphatase is particularly resistant and extremely sensitive compared with other enzymes used for this type of detection, for example peroxidase or glucosidase.

The main advantage of non-radioactive systems and methods is that they may be used diagnostically in an environment where radioactivity could not be employed for routine tests. Such new diagnostic tests, in particular ELISA tests, will replace certain known tests in all areas, particularly bacteriology, virology and parasitology. They may be used in any location where detectable nucleic acids are found, i.e. in living organisms.

The use of non-radioactive ("cold") probes represents an important advance both in fundamental and in clinical research since detection sensitivity is at least equal to that obtained with radioactive isotopes.

Non-radioactive probes are particularly advantageous since they can readily be used without requiring specialized equipment. There are no risks for the operator such as those associated with the use of radioisotopes and, further, they do not require the use of toxic or carcinogenic products.

However, even though they have several advantages over radioactive probes, cold probes do have a number of drawbacks.

Certain of these have already been overcome, as for example in detection of "unique sequences" which is now possible.

One of the major drawbacks of cold probes lies in the fact that the solid supports, e.g. membranes, cannot be used again after hybridization and colorimetric detection. This constitutes a major problem in both clinical and fundamental research.

Researchers must, in fact, reuse the supports, with the target nucleic acids irreversibly fixed thereon, several times, sometimes up to twenty times in some cases.

This is because the fixed nucleic acids may be extremely costly, whether because of their lengthy, costly and difficult extraction or because of their rarity as would be the case with foetal DNA. It is, therefore, important to be able to fix probes on the nucleic acid targets several times, for example by rehybridization.

Such rehybridization is well known with isotopic probes but impossible with cold probes because of the indelible deposit constituted by the colored stain precipitated in situ.

Several attempts have been made to enable the stain produced to be removed, so far without success. In this respect, some manufacturers have advocated the use of hot dimethylformamide to eliminate this indelible stain. Unfortunately dimethylformamide is a volatile teratogenic agent particularly when hot; this limits its use in repeated washes.

Thus, there currently exist no colorimetric detection methods using substrates which produce colored, insoluble products which may be readily eliminated after visualization so that the solid support, to which the nucleic acids to be analyzed are transferred and fixed, may be reused.

One object of the invention is a method for staining nucleic acids fixed on an appropriate solid support, which method constitutes a non-radioactive labelling detection method, the method further comprising elimination of the colored stain produced by the reaction.

Another object of the invention is such a method wherein elimination of the colored stain is obtained using products which are not dangerous to the user.

Another object of the invention is such a method which also produces a good stain and, therefore, good detection of nucleic acids, particularly for staining of unique genome sequences.

Another object of the invention is such a method which may in particular be applied to solid supports constituted by polyamide or nitrocellulose membranes to which the target nucleic acids to be analyzed are irreversibly fixed.

Another object of the invention is a method wherein the solid support, in particular a membrane, may be readily decolorized to produce a perfectly white support without any trace of staining and which may be reused immediately for a new detection operation, for example by hybridization.

Another object of the invention is a set or kit of reactants for carrying out said detection method.

SUMMARY OF THE INVENTION

In one aspect, the invention consists in a method of staining a nucleic acid sequence fixed on a solid support wherein an enzymatic system is employed which fixes to said sequence to detect it by non-radioactive labelling, said enzymatic system is reacted with a chromogenic substrate to form a colored stain which precipitates in situ to reveal directly the sequence detected at the reaction site and a developer solution is employed comprising:

a sulfur-containing organic compound containing a bond with a sulfur atom which constitues a substrate for the enzymatic system and is adapted to be hydrolized by said enzymatic system to form an organic thiol; and a metallic compound which is soluble and stable in aqueous solution and which can react with said organic thiol to form a metal-sulfur compound complex having a characteristic color which precipitates in situ and which may be subsequently decolorized.

Advantageously the metal in the metallic compound is gold, mercury, silver, platinum or lead.

Preferably a gold compound is used which can react with the organic thiol to form a yellow, gold-sulfur compound complex.

In a preferred embodiment of the invention the metal-sulfur compound complex is subsequently reacted with an intensifying compound which accentuates the color of said complex. The color of the complex obtained, even if it is to the human eye visually quite apparent, does not always show up well on photographic film. This is particularly true for the yellow color characteristic of the gold-sulfur compound complex.

According to a further feature of the invention, the metal-sulfur compound complex obtained, whose color may if necessary be intensified, is subsequently treated with a reducing decolorizing solution which allows the support, with the nucleic acid to be analyzed irreversibly fixed thereon, to be reused.

As indicated above, the method of the invention may be used for detecting natural or synthetic, modified or unmodified DNA or RNA which is irreversibly fixed on an appropriate solid support.

These solid supports are well known in the art and may be formed, for example, from polystyrene, latex, etc.

However, in a preferred embodiment of the invention the method is carried out using membranes of polyamide (nylon) or nitrocellulose.

Nucleic acids from the sample to be analyzed are preferably treated with restricting enzymes to fragment them and then transferred to a solid support, using any suitable known technique.

The fragmented nucleic acid may, for example, be disposed in a vessel containing an agarose gel which is then transferred by capillary attraction to the support. Alternatively, the nucleic acid may be directly deposited by using the support as a filter.

In each case the nucleic acid transferred to the support, particularly to a membrane, is irreversibly fixed thereon by drying, ultra-violet treatment or heat treatment, as is well known in the art.

In the subsequent stage of the method of this invention, the solid support having the nucleic acid fixed thereon is treated with an appropriate enzymatic system which may contain a probe nucleic acid sequence complementary to the target nucleic acid sequence held on the solid support. This enzyme must, therefore, be capable of either directly reacting with the probe or the target nucleic acid, or indirectly by means of a conjugate antibody, a protein or any other chemical compound.

In a preferred embodiment of the invention, the enzymatic system used comprises an enzyme having phosphatasic activity, for example alkaline phosphatase, as discussed below.

In this case the developer solution used must comprise an appropriate substrate, for example cystamine-S-phosphate, adenine mononucleotide phosphate or adenosine-5'-monophosphate.

As indicated above, the sulfur organic compound forming the substrate for the enzymatic system is adapted to be hydrolized by the enzyme to form an organic thiol. In the particular case where an alkaline phosphatase enzymatic system is used, the enzyme substrate is a compound having a thioester bond with a phosphate group recognized by the enzyme. Hydrolysis of this bond by the enzyme liberates a phosphate ion and an organic compound having a thiol group, i.e., a compound of type R-SH (where R is an organic radical) which can react with certain metallic compounds which are soluble and stable in aqueous solution to form a metal-sulfur compound complex having a characteristic color.

Instead of an enzymatic system having a phosphatasic enzyme, a system comprising the enzyme glutathion reductase may be employed, subsequently using a substrate of this particular enzyme.

The metallic compound to be used in the instant method must be soluble and stable in aqueous solution and must be able to react with the organic thiol, as indicated above, to form a metal-sulfur compound complex having a characteristic color and which precipitates in situ.

In a preferred embodiment where the metallic compound is a gold compound an organic gold compound or a gold salt may be used.

A gold compound containing Au(I) may therefore be used, i.e. where the gold is in its most common oxidation state. In this form gold produces an insoluble complex with L-cystine in water. The reaction is molar and produces a polymeric-type complex, gold fixation occurring at the cystine sulfur atom.

Few compounds exist which can stabilize gold as Au(I) in aqueous solution. Among these compounds are sodium aurothiomalate (Myocrisine) and aurothioglucose (Solganal RN 12 192-57-3).

In a preferred embodiment of the invention aurothioglucose is used since it is very stable in aqueous solution. It reacts with the thiol group of the hydrolysis product from the enzymatic reaction to form a lemon-to-golden yellow complex which precipitates in situ at the reaction site.

The gold compound used in the developer solution of the invention may also be constituted by a gold salt which is soluble and stable in aqueous solution, for example $HAuCl_4$.

The developer solution used in carrying out the instant method is preferably mixed with an appropriate neutral or slightly basic buffer, for example a Tris-acetate and magnesium acetate buffer.

The developer solution is preferably prepared extemporaneously prior to use by mixing the buffer, the sulfur organic substrate compound and the metallic compound, for example the gold compound.

An aqueous solution is thus obtained which can be used immediately to reveal the nucleic acid sought.

The characteristic color of the metal-sulfur compound complex can be accentuated by treating with an intensifying compound. This compound is preferably a silver salt, for example silver nitrate or silver perchlorate which can react with the complex to produce a brown-black complex. This color is highly visible and shows up particularly well on photographic plates.

The instant process enables the color of the precipitate obtained, with or without intensifier compound, to be eliminated by treatment with a decolorizing solution. According to the invention, this solution is advantageously a mixture of a high concentration of sodium thiosulfate and of ammonium thiosulfate in an acidic medium.

After treatment with the decolorizing solution, the support can be treated with a hot mixture of urea and SDS (sodium dodecyl sulfate) to eliminate all traces of proteins and nucleic acids apart from the nucleic acid sequence remaining fixed on the solid support.

A set or kit of essential reactants may be supplied to carry out the inventive method.

In another aspect the invention consists in a set of reactants for staining a nucleic acid sequence fixed on a solid support wherein an enzymatic system has been used to detect said sequence by non-radioactive labelling, comprising:

a container of a sulfur organic compound containing a bond with a sulfur atom and forming substrate for said enzymatic system, said sulfur organic compound being adapted to be hydrolized by said enzymatic system to produce an organic thiol, a container of a metallic compound which is soluble and stable in aqueous solution and which can react with said organic thiol to produce a metal-sulfur compound complex which precipitates in situ and has a characteristic color, a container of buffer solution which can be mixed with said substrate and metallic compound to form a developer solution, and a container of reducing decolorizing solution, i.e., an aqueous solution of an agent for reducing the metal-sulfur compound.

Preferably this set of reactants additionally contains a container of intensifying solution and a solution of a mixture of urea and SDS.

DESCRIPTION OF THE INVENTION

The invention is further illustrated in the following examples.

EXAMPLE 1

This example used an enzymatic system comprising alkaline phosphatase.

A developer solution was prepared extemporaneously from the following reactants:

| Tris-acetate | 50 mM | pH: 9.5 |
|---|---|---|
| magnesium acetate | 10 mM | |
| cystamine phosphate | 5 mM | |
| aurothioglucose | 3 mM | |

This developer solution was used on a solid support, for example a membrane, on which the nucleic acid to be analyzed had been fixed.

The color developed over a period of between fifteen minutes and two hours depending on the type of hybridization or detection.

Cystamine phosphate is a compound having the formula

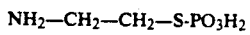

$NH_2—CH_2—CH_2—S-PO_3H_2$ which liberates cystamine of formula

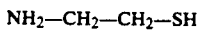

$NH_2—CH_2—CH_2—SH$ following hydrolysis with alkaline phosphatase. Aurothioglucose reacts with the thiol group of cystamine formed by enzymatic hydrolysis of cystamine phosphate to produce a lemon-to-golden-yellow complex which precipitates in situ at the reaction site.

Visibility of modified nucleic acids or nucleic hybrids is accentuated by reacting the aurothioglucose-cystamine complex with silver perchlorate or nitrate to produce a highly visible red-brown-to-black stain.

In the example, a reducing 100 mM solution of silver perchlorate or nitrate was used. Once the aurothioglucose-cystamine complex was judged to have formed sufficiently, the membrane was briefly rinsed with distilled water and the silver salts solution added.

The reaction between the silver and the aurothioglucose-cystamine complex was instantaneous or substantially instantaneous. After the brown staining had developed the membrane was rinsed with distilled water and a photograph could be taken of the results.

Development of the staining is specific to the location where the alkaline phosphate is fixed whether it be held directly by the probe nucleic acid (DNA or RNA) or the target nucleic acid (DNA or RNA) or indirectly by the conjugate antibody, a protein or any other chemical compound.

Sensitivity of the method is equal to that obtained using conventional stains used in disclosing non-radioactive nucleic hybrids. Examples of such stains are 5-bromo-4-chloro-3-indolyl-phosphate (BCIP) and tetrazolium nitroblue (TNB).

The results obtained showed a significant reduction in background interference and better band definition.

The method described above enabled "dot blot" detection down to 1 pg DNA and detection of hybridization of single genome sequences following "Southern" type transfer to the membrane. This comprises imprinting a hydrolyzed nucleic acid which has undergone electrophoresis in agarose gel onto a nitrocellulose or polyamide membrane using a restriction enzyme.

The characteristic staining which appears on the membranes is not indelible and may be removed following observation and photographing.

Decolorization of the membranes was carried out using a reducing decolorizing solution comprising 1 M ammonium thiosulfate, 1 M sodium thiosulfate and 0.1 M sodium acetate, pH 4.8. Alternatively decolorization could be achieved using a rapid fixer for photographic film diluted to quarter strength in a solution of 2 M sodium thiosulfate. The fixer containing sodium hyposulfite and ammonium hyposulfite produced by the French company GUILLEMINOT may be used, for example.

Decolorization was carried out by immersing the membrane in the decolorizing solution for about fifteen minutes at room temperature.

The membrane was then placed in a plastics material bag and a solution of 7 M urea and 1% SDS (100 $\mu l/cm^2$) added. The bag was sealed then immersed for fifteen to thirty minutes in a 70° C. water bath. The membrane was rinsed with distilled water at room temperature, dried then stored between two sheets of whatman paper to prepare it for use in a subsequent detection operation. Storage can be at room temperature.

EXAMPLE 2

This example used an enzymatic system comprising the enzyme glutathion reductase.

This enzymatic system was used to treat a membrane having the nucleic acid to be analyzed transferred to and fixed thereon.

A developer solution was prepared extemporaneously from the following reactants:

| tris-HCl | 50 mM | pH: 7 |
|---|---|---|
| NADPH* | 5 mM | |
| oxidized glutathion (sodium salts) | 5 mM | |
| HAuCL$_4$ or aurothioglucose | 5 mM | |

*NADPH = nicotinamide adenine dinucleotide phosphate, reduced form.

The latter stages of the method were carried out as in example 1.

The method of this invention finds applications in a number of fields, in particular bacteriology, virology and parasitology, greatly improving the performance of known cold probes.

These applications encompass, in particular, detection of genetic illnesses in the foetus using foetal cell samples, diagnostic confirmation of genetic illnesses such as Huntington's disease, determination of paternity, identification of criminals in cases of murder or violence, the study of cancerous cell populations in tumors or the study of RFLP (Restriction Fragment Length Polymorphism) in genetic crossings.

There is claimed:

1. In a method for colorimetric detection of a nucleic acid sequence wherein the nucleic acid sequence is fixed on a solid support and an enzymatic detection system is used to detect the nucleic acid sequence by non-isotopic labelling, the improvement comprising reversibly colorimetrically staining the non-isotopically labelled nucleic acid sequence on the solid support by the sequential steps of:

(a) reacting the non-isotopically labelled nucleic acid sequence with a developer solution comprising a sulfur-containing organic compound containing a bond with a sulfur atom which constitutes a substrate for the enzymatic system and is hydrolyzed by said enzymatic system to form an organic thiol;

(b) reacting with the organic thiol a metallic compound which is soluble and stable in aqueous solution to form a metal-sulfur compound complex having a characteristic color which precipitates in situ and which may subsequently be decolorized; and (c) decolorizing the colorimetrically stained labelled nuclear acid sequence with a reducing agent for the metal-sulfur complex whereby the solid support may be reused.

2. Method according to claim 1 wherein the reducing agent for the metal-sulfur complex is a solution consisting essentially of an acidic mixture of thiosulfate salts.

3. Method according to claim 2 wherein said decolorizing solution comprises a high concentration of sodium thiosulfate and ammonium thiosulfate in an acidic medium.

4. Method according to claim 3 wherein following treatment with said decolorizing solution said support is treated with a hot mixture of urea and sodium dodecyl sulfate to eliminate all traces of proteins and nucleic acids except for the nucleic acid sequence fixed on said solid support.

5. Method according to claim 1 wherein the metal of said metallic compound is selected from the group consisting of gold, mercury, silver, platinum and lead.

6. Method according to claim 5 wherein said metallic compound is a gold compound which can react with said organic thiol to form a yellow gold-sulfur compound complex.

7. Method according to claim 1 wherein said metal-sulfur compound complex is subsequently reacted with an intensifying compound to accentuate the staining of said complex.

8. Method according to claim 1 wherein said enzymatic system comprises a phosphatase enzyme comprising an alkaline phosphatase, and said developer solution comprises a phosphatase substrate, selected from the group consisting of cystamine-S-phosphate, adenine mononucleotide phosphate and adenosine-5'-monophosphate, and a metallic organic compound or a metallic salt.

9. Method according to claim 8 wherein said metallic compound is a gold compound, said enzymatic system comprises alkaline phosphatase and said developer solution comprises cystamine-S-phosphate constituting said phosphatase substrate and aurothioglucose constituting said metallic organic compound.

10. Method according to claim 9 wherein said developer solution comprises:

| Tris-acetate | 50 mM | pH: 9.5 |
|---|---|---|
| magnesium acetate | 10 mM | |
| cystamine-S-phosphate | 5 mM | |
| aurothioglucose | 3 mM | |

11. Method according to claim 1 wherein said enzymatic system comprises the enzyme glutathion reductase and wherein said developer solution comprises a glutathion reductase substrate and a metallic organic compound or a metallic salt.

12. Method according to claim 11 wherein said metallic compound is a gold compound and said developer solution comprises:

| | | |
|---|---|---|
| Tris-HCl | 50 mM | pH: 7 |
| nicotinamide adenine dinucleotide phosphate (reduced form) | 5 mM | |
| oxidized glutathion (sodium salts) | 5 mM | |
| HAuCl₄ or aurothioglucose | 5 mM | |

13. A method according to claim 7 wherein said intensifying compound is a silver salt, comprising silver nitrate, which can react with said metal-sulfur compound complex to produce a brown-black stain.

14. Set of reactants for staining a nucleic acid sequence fixed on a solid support wherein an enzymatic system has been used to detect said sequence by nonisotopic labelling by the method of claim 1, comprising:

a container of a sulfur-containing organic compound containing a bond with a sulfur atom and forming a substrate for said enzymatic system, said sulfur organic compound being adapted to be hydrolyzed by said enzymatic system to produce an organic thiol, a container of a metallic compound which is soluble and stable in aqueous solution and which can react with said organic thiol to produce a metal-sulfur compound complex which precipitates in situ and has a characteristic color, a container of buffer solution which can be mixed with said substrate and metallic compound to form a developer solution, and a container of decolorizing solution consisting essentially of an aqueous solution of a reducing agent for the metal-sulfur complex.

15. Set of reactants according to claim 14 further comprising:

a container of a solution of stain intensifying compound, and a container of a solution of urea and sodium dodecyl sulfate.

16. A set of reactants of claim 14 wherein the container of decolorizing solution is a solution consisting essentially of an acidic mixture of thiosulfate salts.

* * * * *